United States Patent [19]

Monnier

[11] 4,224,940
[45] Sep. 30, 1980

[54] RESPIRATORS

[75] Inventor: Jean-Pierre Monnier, Maurepas, France

[73] Assignee: L'Air Liquide, Societe Anonyme pour l'Etude et l'Exploitation des Procedes Georges Claude, Paris, France

[21] Appl. No.: 923,453

[22] Filed: Jul. 10, 1978

Related U.S. Application Data

[63] Continuation-in-part of Ser. No. 775,440, Mar. 8, 1977, abandoned.

[30] Foreign Application Priority Data

Mar. 19, 1976 [FR] France .......................... 76 07945

[51] Int. Cl.³ .................................... A61M 16/00
[52] U.S. Cl. .......................... 128/205.16; 128/204.25; 128/205.24; 128/205.12
[58] Field of Search ............... 128/145.6, 145.8, 145.5, 128/142.2, 188, 205.16, 204.25, 205.24, 205.12

[56] References Cited

U.S. PATENT DOCUMENTS

| | | | |
|---|---|---|---|
| 2,352,523 | 6/1944 | Emerson | 128/145.8 |
| 2,770,232 | 11/1956 | Falk | 128/145.7 |
| 3,021,839 | 2/1962 | Marsh | 128/142.2 |
| 3,101,708 | 8/1963 | Perry et al. | 128/145.5 |
| 3,503,393 | 3/1970 | Manley | 128/145.6 |

FOREIGN PATENT DOCUMENTS 1008520 10/1965 United Kingdom .
1258071 12/1971 United Kingdom .
1344321 1/1974 United Kingdom .

*Primary Examiner*—Henry J. Recla
*Attorney, Agent, or Firm*—Lee C. Robinson, Jr.

[57] ABSTRACT

A respirator having insufflation and exhalation lines which form a breathing circuit for a patient or other user, insufflation and exhalation valves for admitting and discharging breathable gas to the circuit in accordance with an insufflation phase and an exhalation phase, and a bellows or other storage container which receives breathable gas from a suitable gas generator. The storage container supplies breathable gas to the insufflation line and is connected thereto by a plurality of branch conduits which are arranged such that, during the final portion of the insufflation phase, the pressure in the storage container is lower than the pressure in the breathing circuit.

14 Claims, 10 Drawing Figures

RESPIRATORS

CROSS-REFERENCE TO RELATED APPLICATION

This is a continuation-in-part of co-pending but now abandoned U.S. patent application Ser. No. 775,440 filed Mar. 8, 1977 and now abandoned.

BACKGROUND OF THE INVENTION

The present invention relates to breathing apparatus and more particularly to respirators for supplying breathable gas to a patient or other user.

While of general application, the invention is particularly well suited for use with respirators of the generator type. As is well known, such respirators commonly include a user circuit having a face mask or other breathing apparatus and insufflation and exhalation lines connected to the mask. The insufflation line communicates via an insufflation valve with a compressed gas generator, while the exhalation line communicates with the atmosphere via an exhalation valve. The alternate opening and closing of these valves marks successive insufflation and exhalation phases, the insufflation phase beginning with the opening of the insufflation valve and the simultaneous closing of the exhalation valve, and the exhalation phase beginning with the opening of the exhalation valve and the simultaneous closing of the insufflation valve.

There are at the present time large numbers of such respirators on the market. In some of the respirators currently available the gas generator insufflates the user directly with compressed breathable gas, while in other respirators the insufflation of the breathable gas is performed mechanically by a reservoir which forms a storage container. The respirators are employed, inter alia, to supply breathable gas to sick persons, and they are useful in the home, hospitals, in first aid and so on.

Respirators of the type heretofore employed have exhibited a number of disadvantages. For example, in many prior respirators of the generator type, the user occasionally was subjected to unwanted pressure fluctuations during the insufflation phase, resulting in discomfort and other deleterious effects. In addition, such prior systems frequently required compressors of unnecessarily high capacity in order to accommodate instantaneous input requirements of the user circuit. These and other disadvantages greatly restricted the versatility and reliability of the prior respirators.

SUMMARY

One general object of this invention, therefore, is to provide a new and improved respirator for supplying breathable gas to a user.

More specifically, it is an object of the invention to provide such a respirator in which the pressure supplied to the user is a function of the resistance encountered in the user circuit (air pipe, valve, air passages, bronchi, etc.).

Another object of this invention is to provide a generator-type respirator which permits the use of low power compressors, that is, compressors capable of supplying the necessary quantity of breathable gas during the insufflation phase but not the far greater instantaneous demands of the system.

Still another object of the invention is to provide a respirator which is economical to manufacture and highly versatile and reliable in operation.

To achieve these and other objects, in one illustrative embodiment of the invention there is provided a respirator having a user circuit which includes an insufflation line and an exhalation line. Breathable gas is introduced under pressure through an insufflation valve to the insufflation line from a compressed gas generator or other suitable supply, and an exhalation valve is connected to the exhalation line to vent the exhalation line at the appropriate point in the breathing cycle. The insufflation and exhalation valves are opened and closed at predetermined times during the cycle by a suitable electrical circuit, the opening of the insufflation valve initiating the insufflation phase of the respirator and the opening of the exhalation valve initiating the exhalation phase. As the inhalation valve opens, breathable gas is introduced into the user circuit from a reservoir or storage container communicating with the insufflation line.

In accordance with one feature of the invention, the pressure in the storage container remains lower than the pressure in the user circuit during the final part of the insufflation phase. It is, of course, necessary during this final part of the insufflation phase for the parametric adjustments to be compatible with the breathing characteristics of the user (frequency, volume, ratio of the inhalation time to exhalation time, etc.).

The storage container advantageously is connected to the insufflation line by a conduit arrangement including a plurality of branch conduits in parallel relationship with each other. One of the branches is provided with a regulator valve for admitting breathable gas to the storage container when the pressure in the user circuit is at least equal to the maximum insufflation pressure, and the other branch is provided with a nonreturn valve for preventing the flow of breathable gas from the insufflation line to the storage container.

In several preferred embodiments the insufflation line includes a venturi device. The injector of the venturi device is connected to the compressed gas generator, and the storage container branch conduit containing the nonreturn valve opens into the convergent portion of the venturi. The divergent portion of the venturi communicates with the storage container through the other branch conduit to provide a drop in pressure across the regulator valve which is at least equal to the maximum insufflation pressure during the insufflation phase and which is zero during the exhalation phase. The arrangement is such that the pressure applied to the user during the insufflation phase is a function of the resistance encountered in the user circuit.

In accordance with the invention, in a number of good embodiments, the insufflation valve is closed prior to the opening of the exhalation valve. One advantage of this sequential valve control is to stabilize the pressure in the patient circuit before the start of the exhalation phase.

The present invention, as well as further objects and advantages thereof, will be understood more clearly and fully from the following description of certain preferred embodiments, when read with reference to the accompanying drawings.

DESCRIPTION OF CERTAIN PREFERRED EMBODIMENTS

Figure 1:
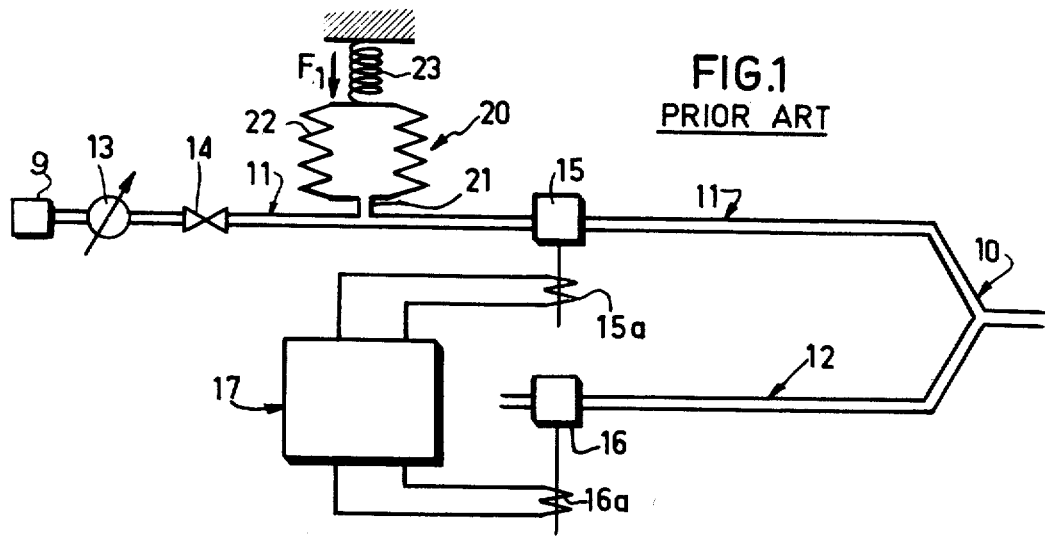
FIG. 1 is a schematic representation of a prior art respirator of the gas generator type.

Referring to the drawings, FIG. 1 shows a respirator of a known kind. This respirator has a compressed gas generator 9 and a patient circuit 10 including an insufflation line 11 and an exhalation line 12. The insufflation line 11 is connected to the generator 9 and includes at least one flowmeter 13 and a regulating valve 14. The exhalation line 12 is vented to the atmosphere.

Two valves 15 and 16 of the "all or nothing" type are arranged in lines 11 and 12, respectively. Each of these valves is adapted to occupy two positions, one open and one closed, in which, respectively, it leaves open its corresponding line or blocks the line completely. The valves 15 and 16 are operated electrically and are associated with an electronic control device 17 of conventional construction. The device 17 is adapted to supply windings 15a and 16a associated with the respective valves 15 and 16 and thereby open and close the valves at preset times in accordance with a predetermined program in which insufflation and exhalation phases alternate. The length and frequency of the phases may be adjusted by adjusting appropriate controls within the device 17.

The respirator of FIG. 1 also includes a reservoir which forms a storage container 20. The storage container 20 is connected by a connecting conduit 21 to the insufflation line 11 between the valve 15 and the generator 9. The container 20 comprises a pneumatic bellows 22 which is provided with a return spring 23. This spring tends to compress the bellows, as shown by arrow F1, to limit its expansion and thereby allow the bellows' internal pressure to raise to a predetermined value.

Figure 2:
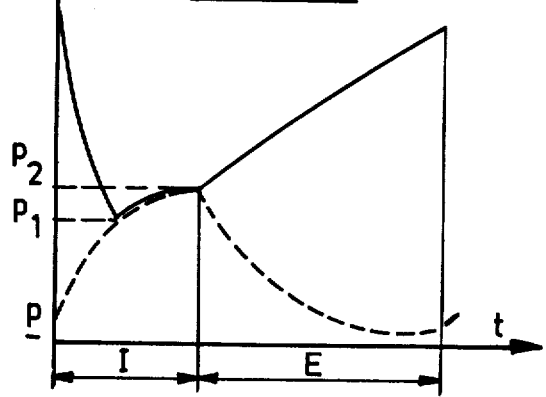
FIG. 2 is a graph showing the changes in pressure during the operation of the respirator of FIG. 1.

The respirator operates in a manner which is shown schematically in the diagram of FIG. 2. At the beginning of the insufflation phase, the insufflation valve 15 is open and the exhalation valve 16 is closed. At the end of this phase, that is to say at the beginning of the exhalation phase, the exhalation valve 16 opens and the insufflation valve 15 closes.

As a function of time (t), the diagram of FIG. 2 illustrates the changes in pressure ($\pi$) in the patient circuit (broken line) and in the storage container (solid line) during the insufflation phases I and the exhalation phases E.

Conditions are assumed to have settled to a steady state. At the beginning of the insufflation (or inhalation) phase, that is to say when the insufflation valve 15 opens and the exhalation valve 16 closes, the pressure in the storage container 20 is at a comparatively high level P. The pressure in the patient circuit 10 is at a substantially lower level p which, by means of a device which is not shown, may be positive, zero, or even negative. In the illustrated example, this value p is positive. The storage container 20 empties to the patient, and its output supplements that from the generator 9, such that the pressure within the container 20 decreases simultaneously with an increase in pressure in the patient circuit. When the pressures in the patient circuit and the storage container are equal ($P_1$), the output from the generator is shared between the patient circuit and the storage container, and the pressure in the latter rises again, with its value remaining the same as that in the patient circuit. The storage container and patient circuit pressures continue to increase to the level ($P_2$), which is reached at the end of the insufflation phase. At that moment the insufflation valve closes and the exhalation valve opens. The patient then breathes out the air contained in his lungs, and the pressure in the patient circuit falls gradually to p, while that in the storage container continues to rise to a level P.

It can be seen from this diagram that the pressure in the storage container is always higher than or equal to the pressure in the patient circuit. At the end of the exhalation phase, the patient circuit is suddenly subjected to a pressure P which may be high, of the order of 100 mbars. This gives rise to a pressure surge effect which is very unpleasant for the patient and may even be more than he can stand.

Figure 3:
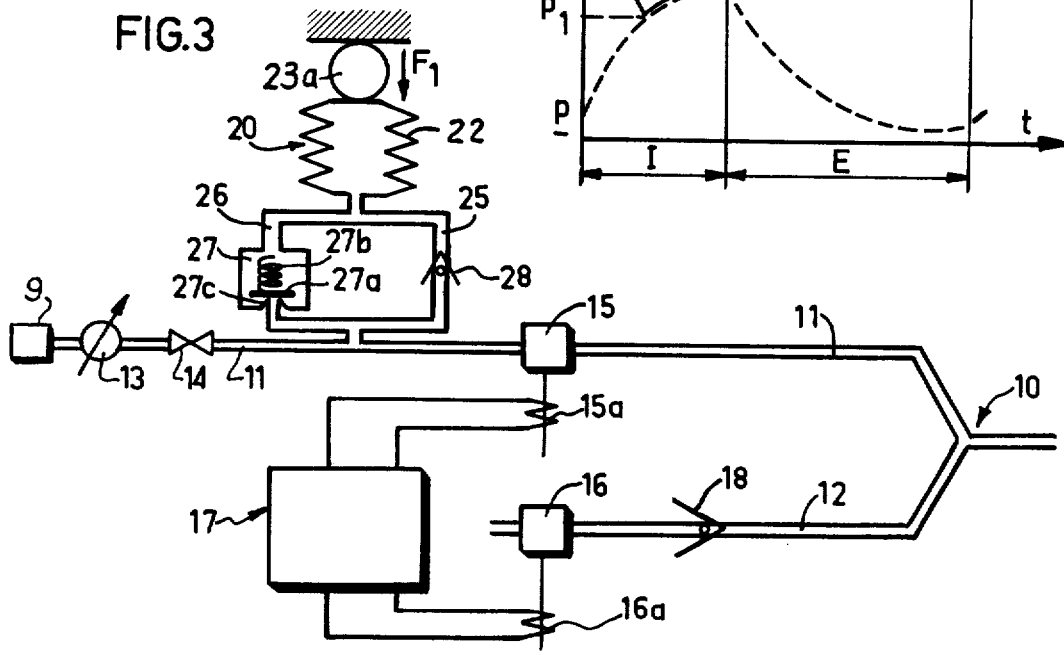
FIGS. 3 and 4 are views similar to FIGS. 1 and 2, respectively, but showing a respirator in accordance with one illustrative embodiment of the invention.

In the embodiment of the invention illustrated in FIG. 3, certain of the components of the generator-type respirator are in general similar to those of FIG. 1, and these components have been given the same reference numerals.

In the FIG. 3 embodiment the conduit arrangement for connecting the bellows 22 to the insufflation line 11 includes two branches 25 and 26. The branch 26 has a pressure regulator type device 27 which comprises a valve member 27a biased by a calibrated spring 27b. The spring 27b urges the valve member 27a toward a seat 27c against the gas pressure in the insufflation line 11.

The regulator device 27 is arranged to allow gas to flow in the direction from the insufflation line 11 to the bellows 22 as soon as the pressure in the line 11 exceeds the thrust of the calibrated spring 27. The drop in pressure across the device 27 is a function of the thrust of the spring 27 and is at least equal to the maximum insufflation pressure, of the order of the approximately 80 mbars. The branch 25 is provided with a nonreturn valve 28 which prevents gas from flowing in the direction from the line 11 to the bellows 22.

Similarly, a nonreturn valve 18 is arranged in the exhalation line 12 to prevent backward flow of air.

As indicated heretofore with respect to the respirator of FIG. 1, the bellows 22 serves as a storage container or reservoir for breathable gas from the generator 9. Rather than using a biasing spring 23 as in FIG. 1, however, the bellows 22 in FIG. 3 is compressed by a flexible bladder 23a. The bladder 23a is inflated to a given pressure and is arranged to exert a predetermined thrust on the bellows in a manner similar to that of the spring 23.

Figure 4:
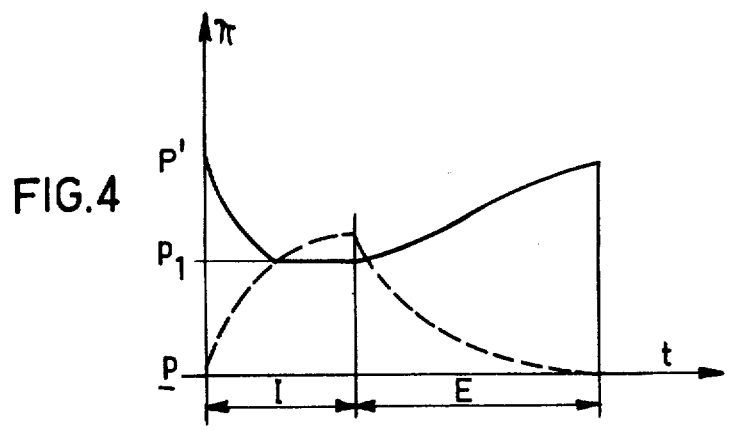

FIG. 4, which is a diagram of the type shown in FIG. 2, illustrates the way in which the arrangement of FIG. 3 operates.

Conditions are once again assumed to have reached a stable state. At the beginning of the insufflation phase of the regulator of FIGS. 3 and 4, the pressure in the storage container 20 is at a level P'. For reasons that will become more fully apparent from the discussion which follows, the pressure P' is less than the pressure P in the prior art regulator of FIG. 2 even though the various pneumatic parameters of the two systems are the same. The pressure in the patient circuit, on the other hand, is at the same level p as in the prior regulator. When the cycle begins, as in the previous case, the storage container 20 empties into the patient circuit 10, and the output from the storage container supplements that from the generator 9.

However, in contrast to the previous regulator, when the pressure in the storage container 20 becomes equal to the pressure in the patient circuit 10 (value $P_1$), the generator then feeds only the patient circuit. The pressure in the patient circuit continues to rise, while the pressure in the storage container remains at level $P_1$. It is only at the end of the insufflation phase, when the insufflation valve 15 closes and the exhalation valve 16 opens, that the patient begins to exhale. The pressure in the patient circuit then gradually falls to level p, and the pressure in the storage container rises to a value of P'.

It will be seen that in the final part of the insufflation phase, after the common pressure $P_1$ has been reached, the pressure in the storage container 20 remains steady at this value, which is lower than the pressure in the patient circuit. When the insufflation valve closes, the pressure on the valve member 27a begins to build up, and as the valve member opens the pressure in the storage container increases to the level P' at a rate which is the same as that in the prior art regulator of FIGS. 1 and 2. Because the increase in storage container pressure begins at a later point in the breathing cycle, however, the storage container pressure P' at the end of the exhalation phase, and hence at the beginning of the inhalation phase, is less than the corresponding pressure P in the prior regulator. With this arrangement, there is a reduction in the pressure surge effect which would otherwise occur because of the excess of the storage container pressure over the patient circuit pressure at the beginning of the insufflation phase.

Figure 5:
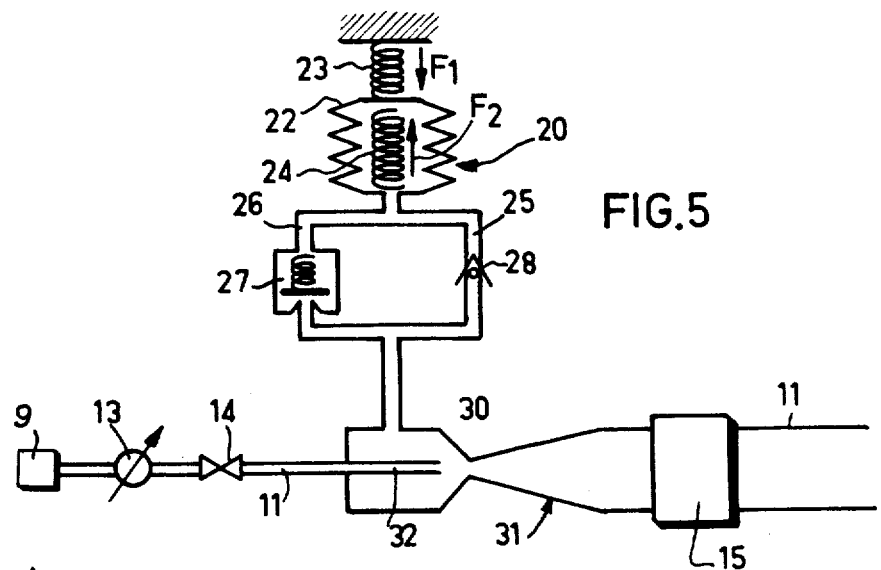
FIG. 5 is a schematic representation similar to a portion of FIG. 1 but showing a respirator in accordance with another illustrative embodiment of the invention.

Another embodiment of a respirator according to the invention is illustrated in FIG. 5. In this latter respirator the storage container 20, which is once again a bellows, is connected to the insufflation line 11 by a double circuit similar to that described above. Although not illustrated in FIG. 5, the exhalation line, the control circuit, etc., may be similar to the corresponding components in FIG. 3.

The storage container 20 opens into the convergent portion 30 of a venturi device 31. The venturi device 31 includes an injector 32 which is fed with breathable gas from the generator 9. The venturi exerts a pumping action on the storage container during the inhalation phase, and thus it facilitates the supply of gas to the patient circuit from the container.

The pumping action of the venturi device 31 on occasion may reduce the pressure within the storage container 20 to less than atmospheric pressure. To prevent the deflation of the bellows 22 during such pressure reductions, the bellows is provided with a compensating spring 24. The spring 24 is located in the interior of the bellows and exerts an upward thrust, as shown by the arrow F2, to hold the bellows in an extended position.

Figure 6:
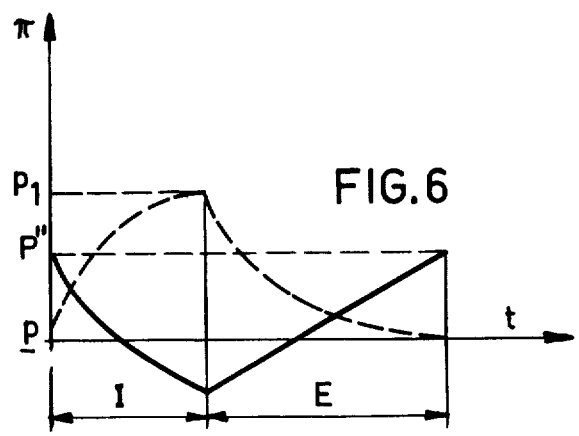
FIG. 6 is a graph showing the changes in pressure during the operation of the respirator of FIG. 5.

FIG. 6, which is similar to FIG. 2 and FIG. 4, illustrates the way in which the apparatus in FIG. 5 operates. At the beginning of the insufflation phase, the pressure in the storage container is P'', and the pressure in the patient circuit is p. Because of the venturi device 31, the pressure P'' is substantially lower than the pressure P in the prior art regulator of FIG. 2. It is also lower than the pressure P' in the regulator of FIG. 4, with a further reduction in the pressure surge effect. Fairly soon after the beginning of the insufflation phase, the storage container pressure drops below the increasing pressure in the patient circuit, and by the end of the insufflation phase it is well below even the lowermost patient circuit pressure. As the insufflation valve closes and the exhalation valve opens, the storage container pressure begins to rise, and the container is inflated from the generator 9 in the manner described heretofore.

The venturi device 31 withdraws breathable gas from the storage container 20 at a comparatively rapid rate. In some cases the rate of withdrawal is sufficient to dispense with the return spring 23 on the bellows 22.

In addition, the regulator of FIG. 5 may be modified by replacing the bellows 22 with a rigid enclosure of substantially increased capacity having the same general characteristics of pressure versus volume. If, for example, the increase in the volume of the bellows 22 is 2 liters for an increase in pressure of 100 mbars, a rigid enclosure having a capacity of 20 liters of water will experience an increase in pressure of approximately 100 mbars if a two liter volume of gas is added to it. Such a modification is useful when there is no restriction on the size of the apparatus, as is the case with so-called "long term" respirators used in hospitals.

Figure 7:
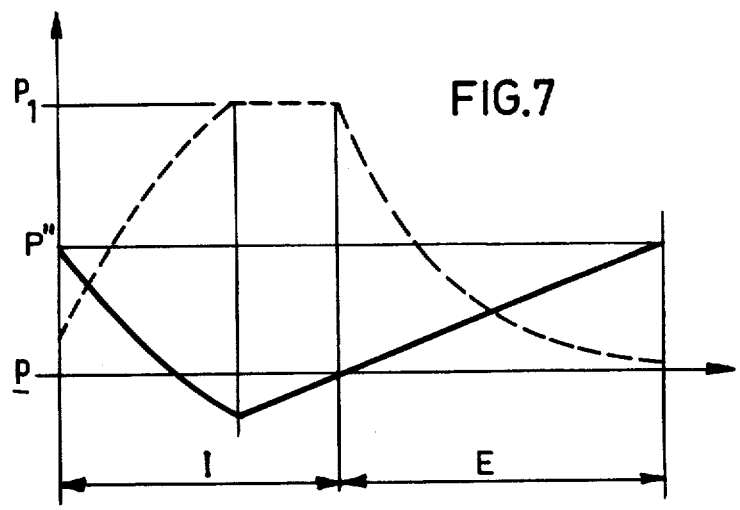
FIG. 7 is a graph showing the changes in pressure during the operation of a modified form of respirator of the type illustrated in FIG. 5.

In the embodiments of the invention described heretofore, the control circuit is effective to open the insufflation valve and close the exhalation valve simultaneously. In other advantageous arrangements, the insufflation valve is closed prior to the opening of the exhalation valve. Referring to FIG. 7, for example, at the beginning of the insufflation phase the insufflation valve is opened and the exhalation valve is closed. The pressure in the storage container is P'' and that in the patient circuit p. During the insufflation phase, the pressure in the storage container drops to a value which is less than ambient pressure because of the pumping action of the venturi, while the pressure in the patient circuit reaches a value $P_1$. At that moment, the insufflation valve closes, and the exhalation valve remains closed. The pressure in the patient circuit then remains practically steady at the value $P_1$ during the last part of the insufflation phase.

There are thus two parts to the insufflation phase. These include an initial active phase characterized by an increase in pressure from p to $P_1$ and a succeeding final phase, termed the "plateau phase", during which the pressure remains substantially equal to $P_1$ and in fact drops slightly by reason of the exchanges taking place in the lungs. Then, as the exhalation valve opens at the beginning of the exhalation phase, the pressure in the patient circuit drops back to p while the pressure in the storage container rises to a value of P''.

In the diagram of FIG. 7 it can be seen that in this case too the pressure level in the storage container is less than that in the patient circuit during the major portion of the cycle.

Figure 8:
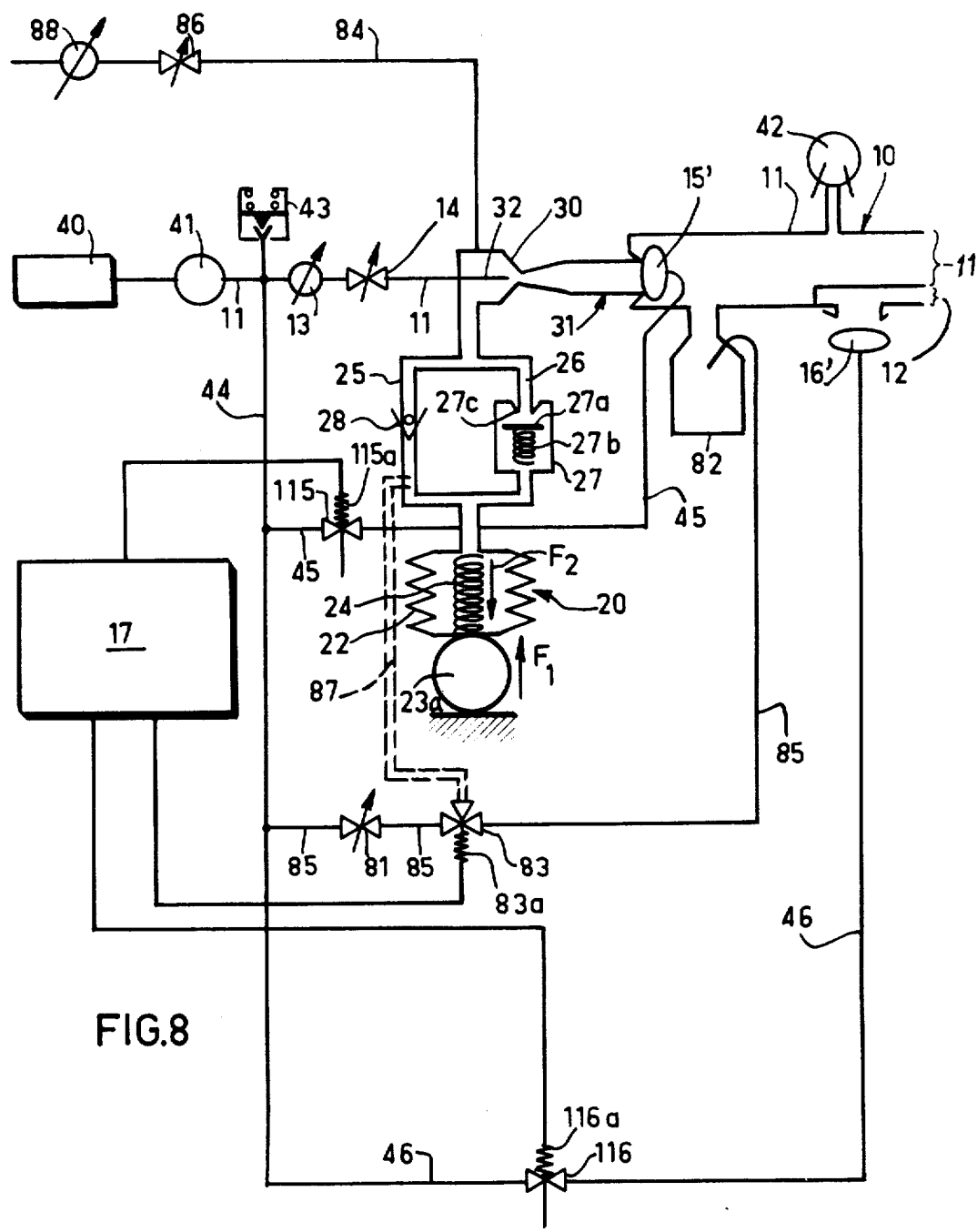
FIG. 8 is a schematic representation similar to FIG. 1 but showing a respirator in accordance with a further illustrative embodiment of the invention.

FIG. 8 shows another embodiment of respirator which is particularly well suited for use as a mobile unit. In this embodiment the electrical valves 15 and 16 have been replaced by pneumatic valves 15' and 16'. The valves 15' and 16' are in turn controlled by three-way electrical valves 115 and 116 having windings 115a and 116a, respectively, which are supplied by the control device 17. Two of the ports of the valve 115 are connected in a conduit 45 which extends between the valve 15' and a control conduit 44 leading to the insufflation line 11, while two of the ports of the valve 116 similarly are connected in a conduit 46 extending between the valve 16' and the conduit 44. The third port of each valve is open to the atmosphere.

Ambient air is compressed by a compressor 41 driven by a motor 40. A pressure regulating valve 43 is connected to the insufflation line 11 on the output side of the compressor 41 to maintain the pressure delivered by the compressor at a constant value. The compressor output is then directed through the flowmeter 13 and the regulator 14 to the injector 32 of the venturi device 31. A pressure gauge 42 may be provided in the line 11 on the downstream side of the venturi to indicate the pressure in the patient circuit.

A spray device or nebulizer 82 is disposed in the inhalation line 11 between the inhalation valve 15' and the pressure gauge 42. The device 82 is supplied with compressed air from the conduit 44 by a duct 85 containing an all or nothing cock 81 and a three-way electrical valve 83. The valve 83 has a winding 83a connected to the control circuit 17 and is opened during the inhalation phase, thus permitting spraying, and closed during the exhalation phase. The third port of the valve 83 is either open to the atmosphere or connected to a line 87 (in dotted lines) leading to the branch conduit 25 between the nonreturn valve 28 and the storage container 20. During the exhalation phase the valve 83 connects the line 85 to the conduit 25 to supply additional air to the storage container 20.

A duct 84 for feeding in pure oxygen or oxygen-enriched air is connected to the induction section of the venturi device 31. The duct 84 is provided with an all or nothing cock 86 and a flowmeter 88 and serves to enrich the air supplied to the patient with oxygen.

Figure 9:
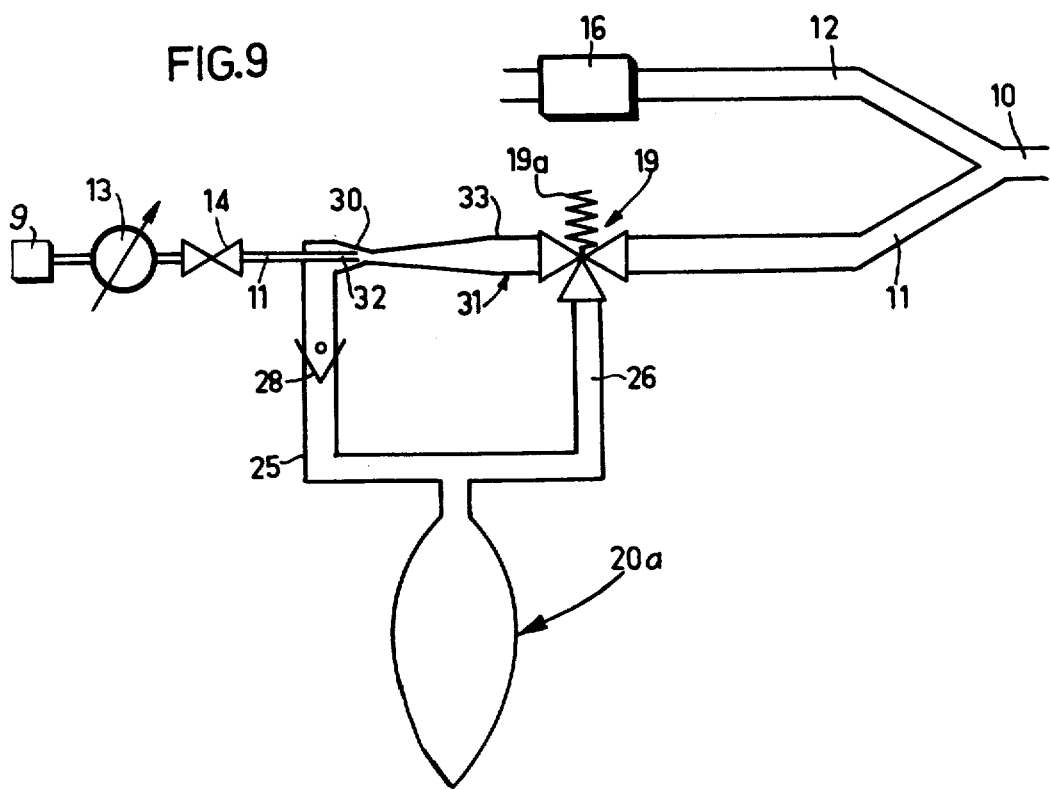
FIG. 9 is a schematic representation similar to a portion of FIG. 1 but showing a respirator in accordance with still another illustrative embodiment of the invention.

In the embodiment of FIG. 9 the insufflation line 11 includes the venturi device 31 having its injector 32 connected to the compressed gas generator 9. The convergent portion 30 of the venturi 31 is connected to a storage container 20a by the branch conduit 25 containing the nonreturn valve 28. The container 20a performs a function similar to that of the storage container 20 described heretofore but is in the form of an expandable bladder of elastic material.

The divergent portion 33 of the venturi 31 is connected to a three-way electrical valve 19 having a winding 19a. During the inhalation phase, the valve 19 connects the venturi 31 with the insufflation line 11 leading to the patient and with the branch conduit 26 when the pressure in the inhalation circuit exceeds a predetermined value. The valve 19 is adjusted so that this value is equal to the maximum insufflation pressure. Thus, the valve causes a drop in pressure which is at least equal to the maximum insufflation pressure during the inhalation phase. During the exhalation phase, the venturi 31 is directly connected to the branch conduit 26. Thus, the valve 19 is substituted for both the valve 15 and the device 27 of the embodiments of FIGS. 3 and 5.

Figure 10:
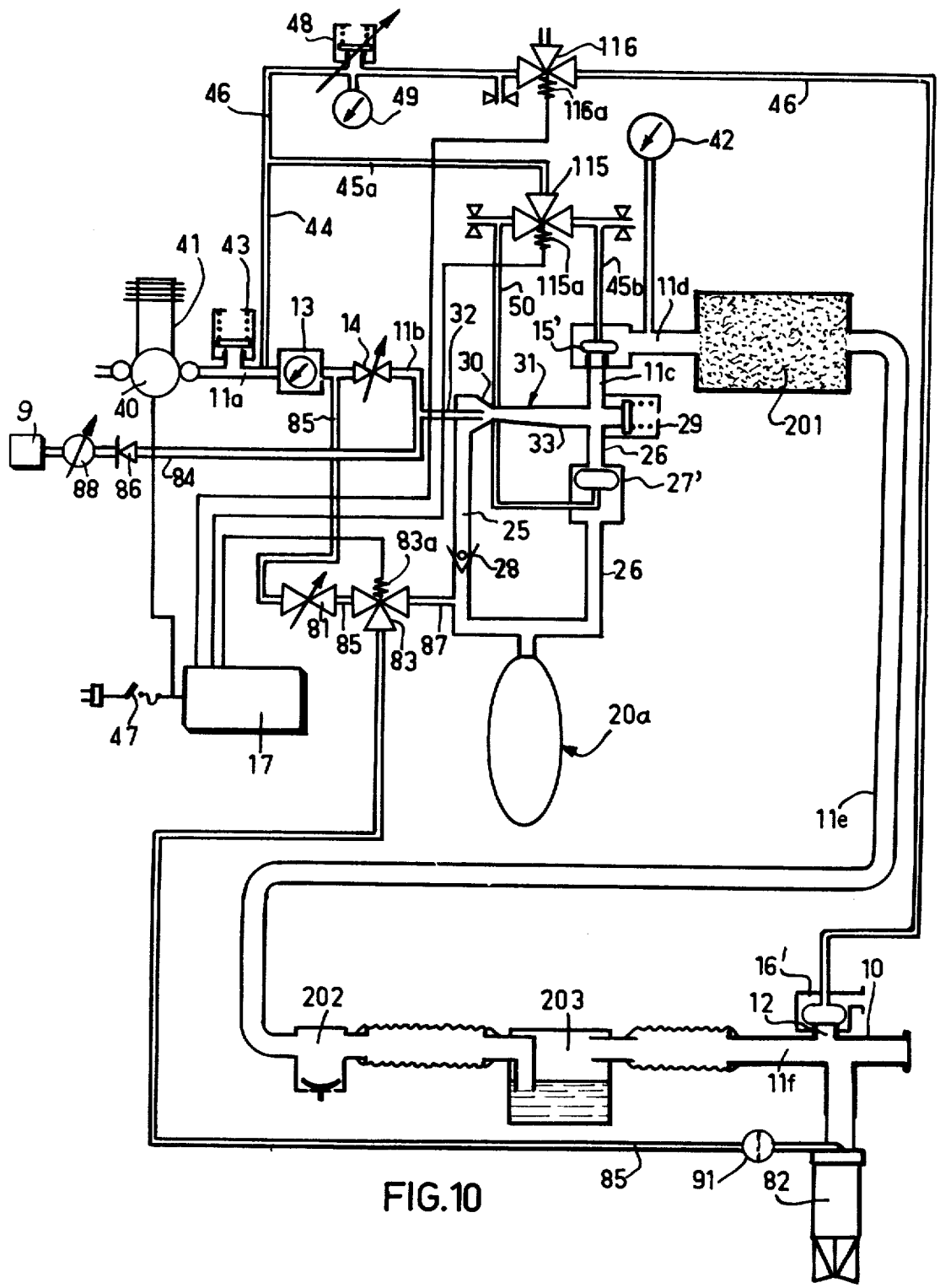
FIG. 10 is a schematic representation similar to FIG. 1 but showing a respirator in accordance with a still further illustrative embodiment of the invention.

FIG. 10 shows a further embodiment of a respirator in accordance with the invention. In this figure the insufflation line is identified by the reference character 11 followed by an alphabetical suffix "a", "b", "c", "d", "e" or "f" to denote the portions or sections of the line between cooperating components. The respirator of the FIG. 10 embodiment contains some complementary units, besides the parts already mentioned and shown in FIG. 8. These include a bacteriological filter 201 between the line sections 11d and 11e and, between the line sections 11e and 11f leading to the patient, a valve 202 for additional air and a cascade humidifier 203. In the line 85 to the spray device 82 (here directly connected to line 11a, below flowmeter 13, instead of to line 44), there is provided a second bacteriological filter shown schematically at 91. The discharge portion of the venturi device 31 includes a safety valve 29. The line 46 to the valve 116 is also provided with a safety valve 48 to relieve excess pressure in the patient circuit. The regulator device 27 in the branch conduit 26 has been replaced by a pneumatic valve 27' controlled by an electric valve 115 through a duct 50. The valve 115 is supplied with pressure over a conduit 45a leading to the line 46a and the line section 11a, and a conduit 45b connects the valve 115 to the valve 27'. The electrical control circuit 17 is connected to an electrical power source through an interruptor 47.

At the beginning of the insufflation phase of the respirator of FIG. 10, the electrical control circuit 17 actuates the valves 115 and 116. The actuation of the valve 115 applies pressure to the pneumatic valve 27', thereby maintaining the valve 27' in its closed position, and releases the pressure at the insufflation valve 15' to open this latter valve. The actuation of the valve 116 serves to close the exhalation valve 16'.

As the insufflation valve 15' opens, compressed air is delivered from the generator 9 through the line sections 11a and 11b to the injector 32 of the venturi device 31. At this point in the operation cycle the pressure in the storage container 20a exceeds that in the line section 11b, and air from the container passes through the valve 28 and the branch conduit 25 to the convergent portion portion of the venturi 31 to supplement that from the generator. The venturi action of the injector 32 and the elasticity of the container 20a serve to augment the rate of introduction of air from the container into the divergent portion 33 of the venturi.

From the venturi 31, the air in the insufflation line passes through the line section 11c, the insufflation valve 15', the line section 11d, the bacteriological filter 201, the line section 11e the valve 202, and the humidifier 203 to the line section 11f leading to the patient.

Simultaneously with the opening of the insufflation valve 15', the electrical circuit 17 operates the valve 83 to supply compressed atmospheric air through the line 85 and the filter 91 to the nebulizer 82 and from the nebulizer to the patient. It is to be noted that the flowmeter 13 indicates the total rate of flow of air to the patient. The valve 202 is normally closed during the insufflation phase, and it opens only in case the patient temporarily needs more air than that delivered by the respirator, or in the event of failure of the respirator. Upon the opening of the valve 202, the insufflation line 202 is vented to permit the introduction of atmospheric air to the patient.

At the end of the insufflation phase, that is to say at the beginning of the exhalation phase, the electrical circuit 17 actuates the valve 115 to feed the insufflation valve 15' and to let air out of the valve 27'. The circuit 17 simultaneously actuates the valve 116 to let air out of the exhalation valve 16'. As a result, the valve 15' closes and the valves 27' and 16' open. The gas exhaled by the patient passes through the valve 16' and escapes into the atmosphere. The air from the venturi 31 feeds the storage container 20 through the valve 27'.

It is to be noted that the storage container 20a performs the function of an automatic mechanical integrator (as it does in the embodiments shown in FIGS. 3, 5, 8 and 9). In effect, if the pumping action of the venturi 30 is not sufficiently effective during the inhalation phase to empty the storage container, that is to say if more breathable gas enters the container during the exhalation phase then leaves it during the inhalation phase, the volume of gas contained in the storage container will increase. The storage container thus stores energy. During the inhalation phase of the succeeding breathing cycle, the stored energy results in an increased discharge from the storage container and hence an increased amount of gas supplied to the patient. In stabilized conditions, by virtue of this stored energy and the pumping action of the venturi, the same quantity of gas leaves the storage container during the inhalation phase as entered it during the preceding exhalation phase.

The amount of energy in the storage container is essentially a function of:
(a) the resistance encountered in the patient's respiratory system (pulmonary compliance);
(b) the rate of flow of breathable gas from the generator;
(c) the rate of breathing (cycles/minute);
(d) the ratio of inhalation time over exhalation time I/E;
(e) the conditions under which the respirator operates, including the pressure loss in the various components and in particular in the valves and circuits, and the induction characteristics of the venturi.

The various parameters of the system are adjusted to provide optimum energy storage in the container in accordance with the particular application for which the respirator is to be used.

The terms and expressions which have been employed are terms of description and not of limitation, and there is no intention in the use of such terms and expressions of excluding any equivalents of the features shown and described or portions thereof, but it is recognized that various modifications are possible within the scope of the invention claimed.

What is claimed is:

1. In a respirator for supplying breathable gas to a user and having an insufflation phase and an exhalation phase, in combination:
   a user circuit including user connection means, an insufflation line having one end connected to said user connection means and an exhalation line having one end connected to said user connection means;
   supply means for introducing breathable gas under pressure to the opposite end of said insufflation line;
   an insufflation valve in the insufflation line;
   an exhalation valve having an inlet connected to the opposite end of said exhalation line and an outlet communicating with the atmosphere;
   control means connected to the insufflation valve and the exhalation valve for opening and closing said valves at predetermined times, the opening of the insufflation valve initiating the insufflation phase and the opening of the exhalation valve initiating the exhalation phase;
   a reservoir forming a storage container for breathable gas from the supply means, means for maintaining the gas in the reservoir at a predetermined pressure greater than the pressure within the insufflation line at the beginning of the insufflation phase;
   conduit means including a pair of branch conduits connected in parallel relationship between the storage container and the insufflation line upstream of the insufflation valve, unidirectional flow means in one of said branch conduits for supplying breathable gas from said storage container to the user circuit during the insufflation phase; and
   unidirectional flow means in said other branch conduit responsive to the maximum insufflation pressure in said insufflation line for supplying breathable gas to said reservoir when said maximum insufflation pressure is reached, whereby the pressure in said container is maintained lower than that in said circuit during the final portion of the insufflation phase and the initial portion of the exhalation phase.

2. In a respirator for supplying breathable gas to a user and having an insufflation phase and an exhalation phase, in combination:
   a user circuit including user connection means, an insufflation line having one end connected to said user connection means, and an exhalation line having one end connected to said user connection means;
   supply means for introducing breathable gas under pressure to the opposite end of said insufflation line;
   an insufflation valve in the insufflation line;
   an exhalation valve having an inlet connected to the opposite end of said exhalation line and an outlet communicating with the atmosphere;
   control means connected to the insufflation valve and the exhalation valve for opening and closing said valves, the opening of the insufflation valve initiating the insufflation phase and the opening of the exhalation valve initiating the exhalation phase, said control means closing the insufflation valve prior to the opening of the exhalation valve during each breathing cycle;
   a reservoir forming a storage container for breathable gas from the supply means, means for maintaining the gas in the reservoir at a predetermined pressure greater than the pressure within the insufflation line at the beginning of the insufflation phase;
   conduit means interconnecting the storage container and the insufflation line upstream of the insufflation valve for supplying unidirectional flow of the breathable gas from said storage container to the user circuit during the insufflation phase; and
   unidirectional flow means connected in the conduit means and responsive to the maximum insufflation pressure in said insufflation line for supplying breathable gas to said reservoir when said maximum insufflation pressure is reached, whereby the pressure in said container is maintained lower than that in said circuit during the final portion of the insufflation phase and the initial portion of the exhalation phase.

3. In a respirator for supplying breathable gas to a user and having an insufflation phase and an exhalation phase, in combination:
  a user circuit including user connection means, an insufflation line having one end connected to said user connection means and an exhalation line having one end connected to said user connection means;
  supply means for introducing breathable gas under pressure to the opposite end of said insufflation line;
  an insufflation valve in the insufflation line;
  an exhalation valve having an inlet connected to the opposite end of said exhalation line and an outlet communicating with the atmosphere;
  control means connected to the insufflation valve and the exhalation valve for opening and closing said valves at predetermined times, the opening of the insufflation valve initiating the insufflation phase and the opening of the exhalation valve initiating the exhalation phase;
  a reservoir forming a storage container for breathable gas from the supply means
  means for maintaining the gas in the reservoir at a predetermined pressure greater than the pressure within the insufflation phase; and
  conduit means including a pair of branch conduits connected in parallel relationship between the storage container and the insufflation line upstream of the insufflation valve for supplying breathable gas from said storage container to the user circuit during the insufflation phase and for maintaining the pressure in said container lower than that in said circuit during the final portion of the insufflation phase and the initial portion of the exhalation phase, one of said branch conduits having a regulator valve for admitting breathable gas to the storage container when the pressure in said circuit is at least equal to the maximum insufflation pressure, and the other of said branch conduits having a nonreturn valve for preventing the flow of breathable gas from the insufflation line to the storage container.

4. In a respirator for supplying breathable gas to a user and having an insufflation phase and an exhalation phase, in combination:
  a user circuit including user connection means, an insufflation line having one end connected to said user connection means and an exhalation line having one end connected to said user connection means;
  supply means for introducing breathable gas under pressure to the opposite end of said insufflation line;
  an insufflation valve in the insufflation line;
  an exhalation valve having an inlet connected to the opposite end of said exhalation line and an outlet communicating with the atmosphere;
  control means connected to the insufflation valve and the exhalation valve for opening and closing said valves at predetermined times, the opening of the insufflation valve initiating the insufflation phase and the opening of the exhalation valve initiating the exhalation phase;
  a reservoir forming a storage container for breathable gas from the supply means, means for maintaining the gas in the reservoir at a pressure greater than the pressure within the insufflation line at the beginning of the insufflation phase; and
  conduit means including a pair of branch conduits connected in parallel relationship between the storage container and the insufflation line upstream of the insufflation valve for supplying breathable gas from said storage container to the user circuit during the insufflation phase and for maintaining the pressure in said container lower than that in said circuit during the final portion of the insufflation phase and the initial portion of the exhalation phase, one of said branch conduits having a regulator valve for admitting breathable gas to the storage container when the pressure in said circuit is at least equal to the maximum insufflation pressure, and the other of said branch conduits having a nonreturn valve for preventing the flow of breathable gas from the insufflation line to the storage container.

5. In a respirator as defined in claim 4, said storage container comprising a compressible bellows; and spring means for exerting a continuous compressive force on the bellows.

6. In a respirator as defined in claim 4, in which said storage container comprises a bladder of elastic material.

7. In a respirator for supplying breathable gas to a user and having an insufflation phase and an exhalation phase, in combination:
  a user circuit including connection means, an insufflation line and an exhalation line connected to said user connection means;
  venturi means having a discharge portion communicating with the insufflation line and an injector portion;
  supply means for introducing breathable gas under pressure to the injector portion of the venturi means;
  an insufflation valve in the insufflation line;
  an exhalation valve in the exhalation line;
  control means connected to the insufflation valve and the exhalation valve for opening and closing said valves at predetermined times, the opening of the insufflation valve initiating the insufflation phase and the opening of the exhalation valve initiating the exhalation phase;
  a reservoir forming a storage container for breathable gas from the supply means, means for maintaining the gas in the reservoir at a predetermined pressure greater than the pressure within the insufflation line at the beginning of the insufflation phase;
  conduit means interconnecting the storage container and the venturi means upstream of the insufflation valve for supplying unidirectional flow of breathable gas from said storage container to the user circuit during the insufflation phase; and
  unidirectional flow means connected to the conduit means and responsive to the maximum insufflation pressure in said insufflation line for supplying breathable gas to said reservoir when said maximum insufflation pressure is reached, whereby the pressure in said container is maintained lower than that in said circuit during the final portion of the insufflation phase and the initial portion of the exhalation phase.

8. In a respirator for supplying breathable gas to a user and having an insufflation phase and an exhalation phase, in combination:
 a user circuit including user connection means, an insufflation line and an exhalation line connected to said user connection means;
 venturi means having a discharge portion communicating with the insufflation line and an injector portion;
 supply means for introducing breathable gas under pressure to the injector portion of the venturi means;
 an insufflation valve in the insufflation line;
 an exhalation valve in the exhalation line;
 control means connected to the insufflation valve and the exhalation valve for opening and closing said valves, the opening of the insufflation valve initiating the insufflation phase and the opening of the exhalation valve initiating the exhalation phase;
 a reservoir forming a storage container for breathable gas from the supply means for maintaining the gas in the reservoir at a predetermined pressure greater than the pressure within the insufflation line at the beginning of the insufflation phase; and
 conduit means including a pair of branch conduits connected in parallel relationship between the storage container and the venturi means upstream of the insufflation valve for supplying breathable gas from said storage container to the user circuit and for maintaining the pressure in said container lower than that in said circuit during the final portion of the insufflation phase and the initial portion of the exhalation phase, one of said branch conduits having a regulator valve for admitting breathable gas to the storage container when the pressure in said circuit is at least equal to the maximum insufflation pressure, and the other of said branch conduits having a nonreturn valve for preventing the flow of breathable gas from the venturi means to the storage container.

9. In a respirator as defined in claim 8, the venturi means including a divergent section connected to said one branch conduit and a convergent section connected to said other branch conduit.

10. In a respirator as defined in claim 8, the venturi means including a divergent section communicating with said insufflation line and a convergent section communicating with each of said branch conduits.

11. In a respirator for supplying breathable gas to a user and having an insufflation phase and an exhalation phase, in combination:
 a user circuit including user connection means, an insufflation line and an exhalation line connected to said user connection means;
 venturi means having a convergent portion, a divergent portion communicating with the insufflation line, and an injector portion;
 means including a compressed gas generator for introducing breathable gas under pressure to the injector portion of the venturi means;
 an insufflation valve in the insufflation line;
 an exhalation valve in the exhalation line;
 control means connected to the insufflation valve and the exhalation valve for opening and closing said valves at predetermined times, the opening of the insufflation valve initiating the insufflation phase and the opening of the exhalation valve initiating the exhalation phase;
 a reservoir forming a storage container for breathable gas from the generator, means for maintaining the gas in the reservoir at a predetermined pressure greater than the pressure within the insufflation line at the beginning of the insufflation phase; and
 conduit means including a pair of branch conduits connected in parallel relationship between the storage container and the convergent portion and divergent portion of the venturi means, respectively, and upstream of the insufflation valve for supplying breathable gas from said storage container to the user circuit and for maintaining the pressure in said container lower than that in said circuit during the final portion of the insufflation phase and the initial portion of the exhalation phase, one of said branch conduits connected between the convergent portion and said storage container having unidirectional flow means for preventing the flow of breathable gas from said convergent portion to the storage container, the other of said branch conduits connected between the divergent portion and the storage container including unidirectional flow means responsive to the maximum insufflation pressure in said insufflation line for supplying breathable gas to said reservoir when said maximum insufflation pressure is reached.

12. In a respirator as defined in claim 11, which further comprises, in combination:
 nebulizer means connected to the insufflation line; and
 means including a supply conduit for introducing breathable gas from said generator to said nebulizer means simultaneously with the opening of said insufflation valve.

13. In a respirator for supplying breathable gas to a user and having an insufflation phase and an exhalation phase, in combination:
 a user circuit including user connection means, an insufflation line and an exhalation line connected to said user connection means;
 venturi means having a convergent portion, a divergent portion communicating with the insufflation line, and an injector portion;
 means including a compressed gas generator for introducing breathable gas under pressure to the injector portion of the venturi means;
 an insufflation valve in the insufflation line;
 an exhalation valve in the exhalation line;
 control means connected to the insufflation valve and an exhalation valve for opening and closing said valves, the opening of the insufflation valve initiating the insufflation phase and the opening of the exhalation valve initiating the exhalation phase, said control means closing the insufflation valve prior to the opening of the exhalation valve during each breathing cycle;
 a reservoir forming a storage container for breathable gas from the generator, means for maintaining the gas in the reservoir at a predetermined pressure greater than the pressure within the insufflation line at the beginning of the insufflation phase; and
 conduit means including a plurality of branch conduits interconnecting the storage container and the venturi means upstream of the insufflation valve for supplying breathable gas from said storage container to the user circuit during the insufflation phase; and means connected to the conduit means for maintaining the pressure in said container lower than that in said circuit during the final portion of the insufflation phase and the initial portion of the exhalation phase, one of said branch conduits having a regulator valve for admitting breathable gas to the storage container during the exhalation phase and when the pressure in said circuit is at least equal to the maximum insufflation pressure during the insufflation phase, and the other of said branch conduits communicating with the convergent portion of the venturi means and having a nonreturn valve for preventing the flow of breathable gas from said convergent portion to the storage container.

14. In a respirator for supplying breathable gas to a user and having an insufflation phase and an exhalation phase, in combination:
- a user circuit including user connection means, an insufflation line and an exhalation line connected to said user connection means;
- venturi means having a convergent portion, a divergent portion communicating with the insufflation line, and an injector portion;
- a compressed gas generator for introducing breathable gas under pressure to the injector portion of the venturi means;
- a pneumatically operated insufflation valve in the insufflation line;
- a pneumatically operated exhalation valve in the exhalation line for connecting the same to the atmosphere;
- control means connected to the insufflation valve and the exhalation valve for automatically applying pressure thereto from said generator at predetermined times, to open and close said valves, the opening of the insufflation valve initiating the insufflation phase and the opening of the exhalation valve initiating the exhalation phase;
- a reservoir forming a storage container for breathable gas from the generator; and
- conduit means including a plurality of branch conduits interconnecting the storage container and the venturi means upstream of the insufflation valve for supplying breathable gas from said storage container to the user circuit and for maintaining the pressure in said container lower than that in said circuit during the final portion of the insufflation phase and the initial portion of the exhalation phase, one of said branch conduits being connected to the divergent portion of the venturi means and having a regulator valve for admitting breathable gas from said divergent portion to the storage container when the pressure in said circuit is at least equal to the maximum insufflation pressure, and the other of said branch conduits being connected to the convergent portion of the venturi means and having a nonreturn valve for preventing the flow of breathable gas from said convergent portion to the storage container.

* * * * *